United States Patent [19]

Page, Jr. et al.

[11] 4,167,062
[45] Sep. 11, 1979

[54] DENTAL HANDPIECE

[75] Inventors: Joe W. Page, Jr., Huntington Beach; Paul H. Stahlhuth, Mission Viejo, both of Calif.

[73] Assignee: Den-Tal-Ez Mfg. Co., West Des Moines, Iowa

[21] Appl. No.: 825,961

[22] Filed: Aug. 19, 1977

[51] Int. Cl.² .......................... A61C 1/10; A61C 1/12; B23B 5/22; F03B 13/04
[52] U.S. Cl. ...................... 32/26; 279/1 Q; 415/503
[58] Field of Search .......................... 32/26; 415/503; 279/1 Q, 50

[56] References Cited
U.S. PATENT DOCUMENTS

| | | | |
|---|---|---|---|
| 1,835,961 | 12/1931 | Pieper | 32/26 |
| 2,693,631 | 11/1954 | Redman | 279/50 |
| 3,494,364 | 2/1970 | Peters | 279/1 Q |
| 3,530,586 | 9/1970 | Weickgenannt | 32/26 |
| 4,040,311 | 8/1977 | Page, Jr. et al. | 415/503 |

Primary Examiner—Louis G. Mancene
Assistant Examiner—Michael J. Foycik
Attorney, Agent, or Firm—Rudolph L. Lowell

[57] ABSTRACT

A straight dental handpiece has a tubular housing for a motor driven collet mechanism rotatably supported at one end of the housing. The burr receiving collet mechanism is actuated by a pair of diammetrically opposed cams supported for rotational movement about an axis extended transversely of the housing. In response to rotation of the cams, a cam follower on the collet mechanism is axially moved to actuate the collet mechanism to a burr receiving position. The cams are rotated by an external lever on the housing that is pivotally movable from a longitudinally extended operating position in nested relation with the housing, wherein the burr is gripped in the collet mechanism, to a burr releasing position projected generally radially of the housing.

6 Claims, 12 Drawing Figures

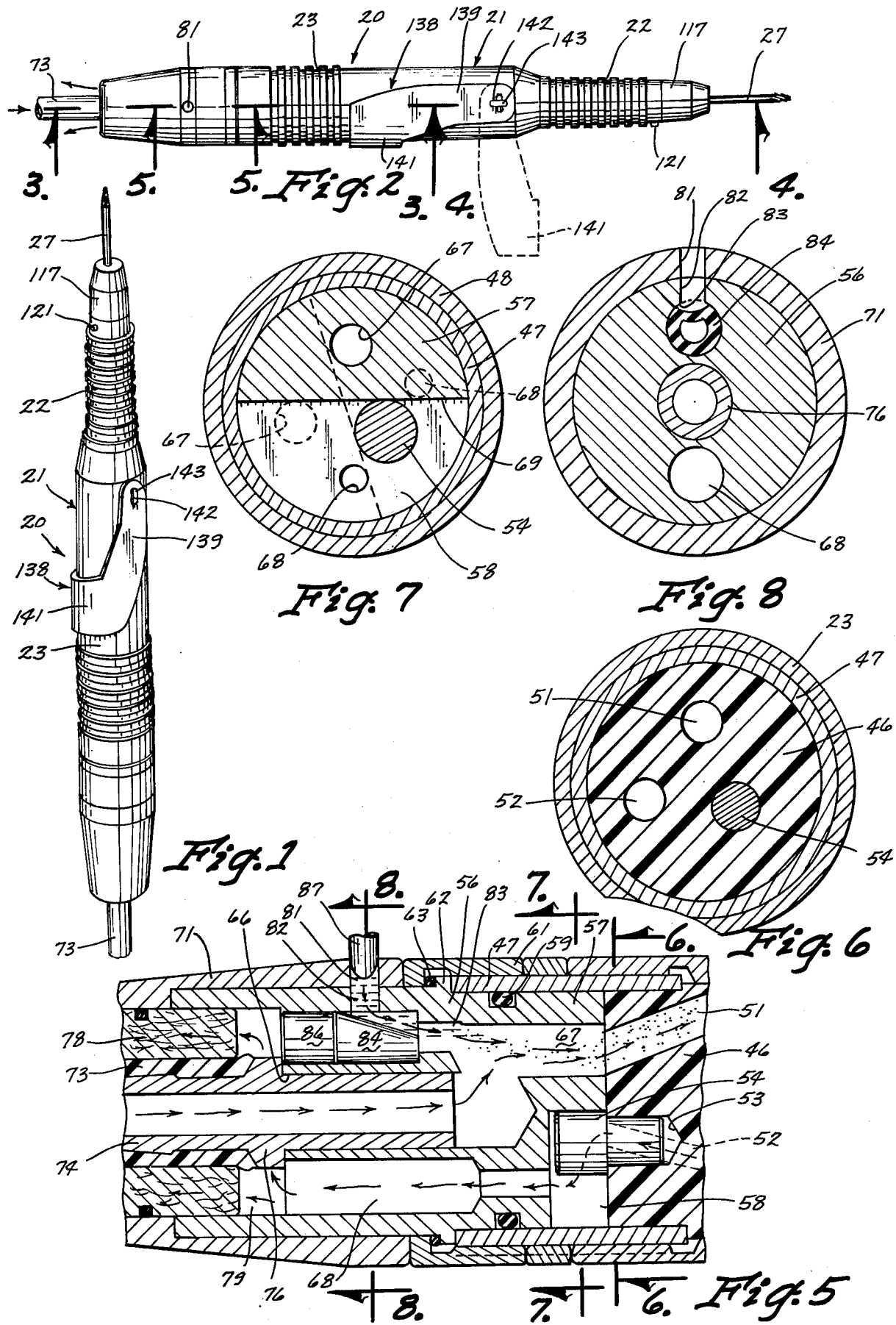

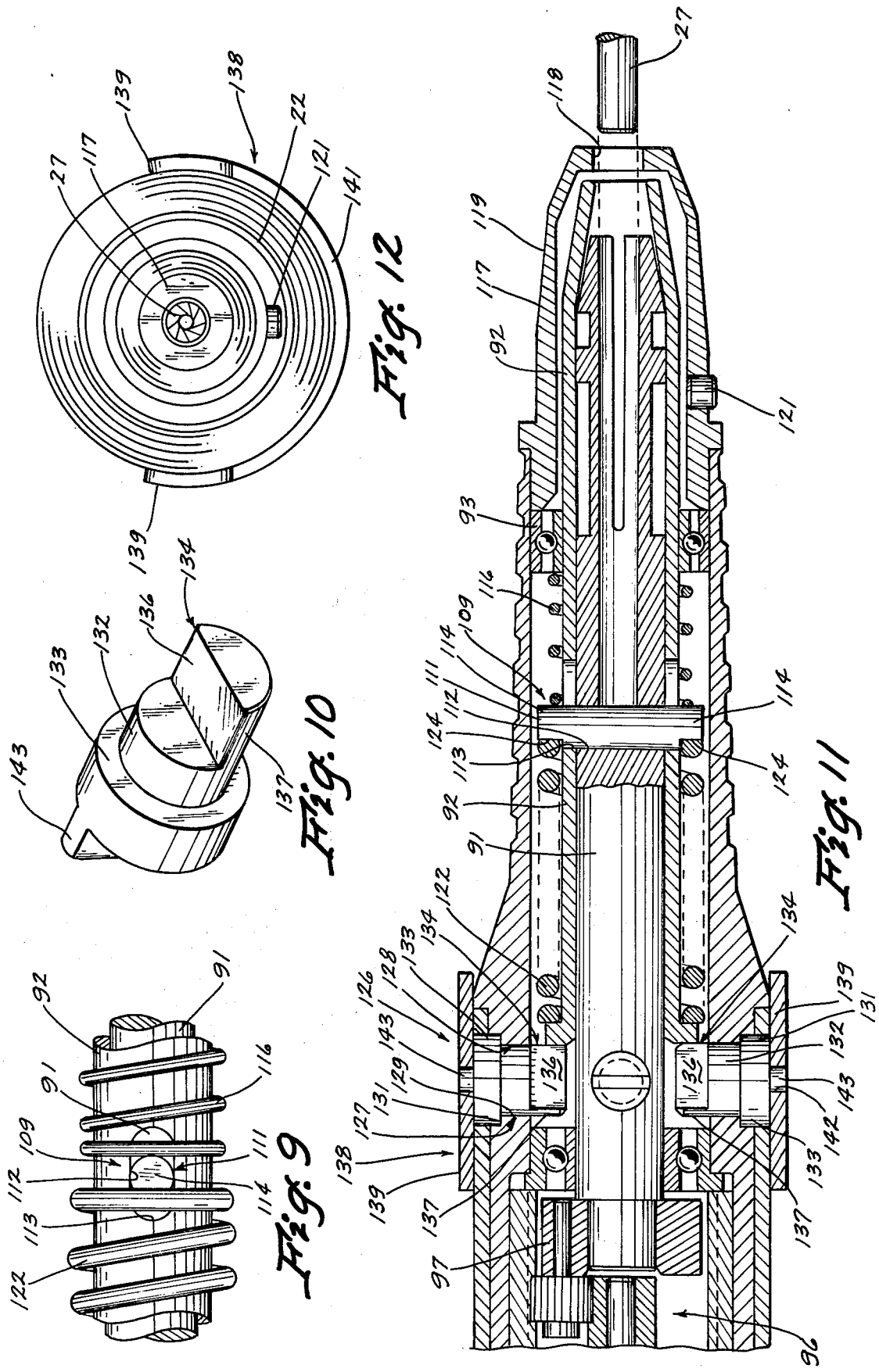

4,167,062

DENTAL HANDPIECE

SUMMARY OF THE INVENTION

The collet actuating mechanism in the dental handpiece of the present invention is of a simple and rugged construction and operable with one hand without the use of tools. The saddle shaped lever for rotating the diammetrically opposed cams is movable from a burr gripping or operating position in nested relation with the housing to a burr release or collet opening position projected generally radially of the housing, thereby eliminating operator interference when the handpiece is in use and providing a positive visual indication as to the open or closed condition of the collet mechanism. The lever is reversible for right or left hand operation and provides sufficient leverage for easily opening the collet mechanism against the heavy spring pressure which assures a positive gripping action on a burr. In the operating position of the lever, the cross sectional arcuate contour thereof affords a light spring grip or snap-fit on the housing. When the lever is pivoted to open the collet mechanism, the pressure of the collet spring is directed centrally of the cams so as to substantially eliminate any snap action of the lever to its collet opening position. Likewise, the frictional engagement between the cams and cam follower, when the lever is in its collet opening position, is effective to stop the handpiece motor, so as to protect against operator injury and chuck damage.

BRIEF DESCRIPTION OF THE DRAWINGS

FIG. 1 is a perspective view of the dental handpiece of the invention showing a dental burr engaged in the collet mechanism;

FIG. 2 is a side elevational view of the dental handpiece shown in FIG. 1;

FIG. 5 is an enlarged longitudinal sectional view taken along line 5—5 in FIG. 2, showing an external lubricating port for the handpiece;

FIG. 6 is a transverse sectional view, as seen on line 6—6 in FIG. 5, showing the air passages through a stationary valve plate of the handpiece;

FIG. 7 is a transverse sectional view, as seen on line 7—7 in FIG. 5, showing the changed positions of the rotatable valve body and air passages therethrough;

FIG. 8 is a transverse sectional view, on line 8—8 in FIG. 5, showing the external lubricating port for the handpiece;

FIG. 9 is a detail view of a pin and slot connection between the collet shaft and sleeve, taken along line 9—9 in FIG. 4;

FIG. 10 is an enlarged detail perspective view of one of the collet actuating cams of the invention;

FIG. 11 is a longitudinal sectional view, similar to FIG. 4, showing the collet mechanism in an open position for receiving a dental burr; and FIG. 12 is a front view of the handpiece of the invention.

DETAILED DESCRIPTION OF THE INVENTION

Figure 3:
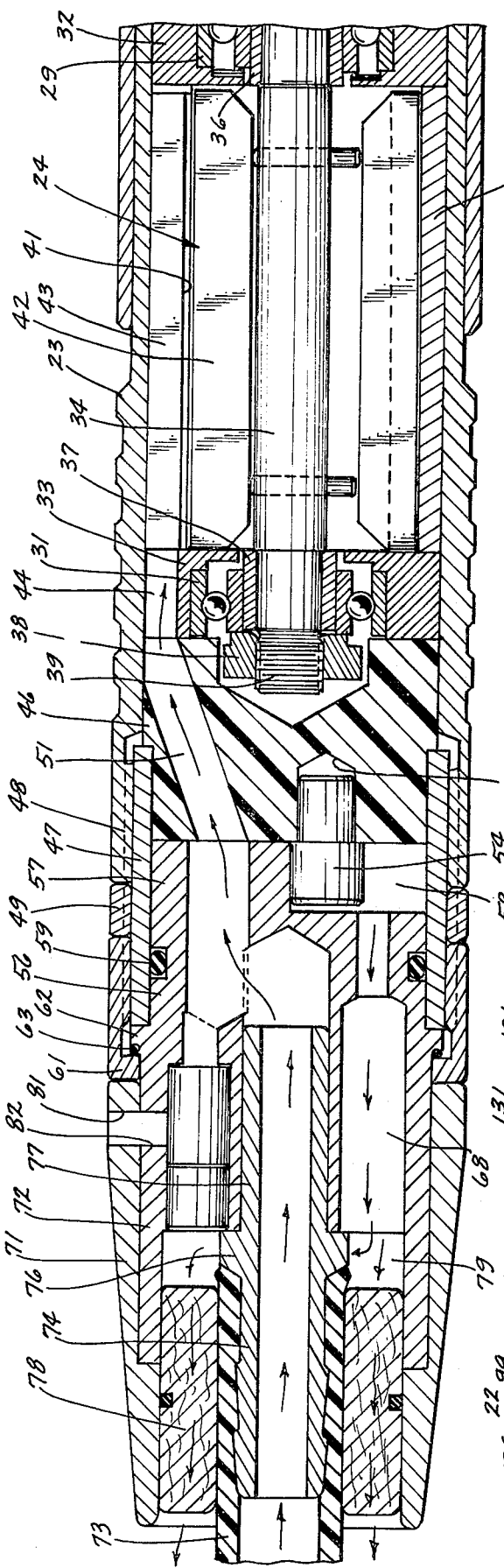
FIG. 3 is an enlarged longitudinal sectional view of the rear section of the handpiece, as seen on line 3—3 in FIG. 2.

The straight dental handpiece of the present invention, indicated generally at 20 in FIGs. 1 and 2, includes an elongated tubular housing 21 having forward and rearward housing portions 22 and 23, respectively. A vane type air motor, indicated at 24 in FIG. 3 is supported within the rearward housing portion 23 in a driving relation with a collet mechanism, indicated at 26 in FIG. 4, which is rotatably supported in the forward housing portion 22. A dental burr 27 is insertable through the forward end of the housing 21 for reception into the collet mechanism 26.

The vane type air motor 24, FIG. 3, includes a cylinder or stator 28 secured within the rearward housing portion 23 between front and rear motor bearings 29 and 31, respectively, which are fitted within respective bearing housings 32 and 33. A cylindrical rotor 34, having front and rear bearing sleeves 36 and 37 secured on opposite end portions thereof, is rotatably supported within the bearings 29 and 31. A rotor nut 38 is tightened onto an externally threaded rear end portion 39 of the rotor 34 for securing the rotor axially of the motor bearing 31.

The stator 28 has a bore 41 with an axis eccentric to the coincident axes of the rearward housing portion 23 and motor bearings 29 and 31. Three pairs of elongated vanes 42 are rotatable with the rotor 34 and movable radially thereof within the eccentric bore 41 as the rotor 34 is rotated.

To convey air to the motor for reversibly driving the rotor, two longitudinally extended passages 43, only one of which is shown in FIG. 2, are formed in the stator 28. Corresponding passages 44 in the rear bearing housing 33 provide fluid communication to the passages 43 through the bearing housing 33. For a detailed description of the structure and operation of the vane type air motor 24, reference is made to U.S. Pat. No. 3,942,392.

Air is conveyed to and from the passages 44 and 43 through a valve plate 46 which is axially secured against the rear bearing housing 33 by an externally threaded coupling 47 engageable with an internally threaded rear end seciton 48 of the rear housing portion 23. A lock ring 49 secures the coupling 47 in its threaded position.

The valve plate 46 has a pair of forwardly and outwardly inclined passages 51 and 52, FIGS. 5 and 6, extended longitudinally therethrough for communication with respective ones of the motor air passages 43. A bore 53 in the rear end of the valve plate 46 supports a stop pin 54.

To direct air to one of the valve plate passages 51 or 52 and to provide an exit for the exhaust air from the motor through the other passage, a reversing valve 56, FIG. 5, is inserted into the coupling 47 with a semicylindrical shaped forward extension 57 bearing against the valve plate 46 in sealing engagement therewith. The stop pin 54 is thus situated within a semicylindrical shaped exhaust chamber 58 formed between the reversing valve 56 and valve plate 46 opposite extension 57. The reversing valve 56 is sealed within the coupling 47 by an O-ring 59 and is retained axially of the coupling by a retaining ring 61 acting through a resilient washer 63 against an external annular flange 62 on the reversing valve 56.

Air enters the reversing valve 56 through the rear end of a central inlet passage 66 having a forward end open to a bore 67 through the forward extension 57. An exhaust passage 68 extends longitudinally through the reversing valve 56 and opens at its forward end into the exhaust chamber 58.

Reversing valve 56 is pivotally movable within the coupling 47 between the solid and dotted line positions shown in FIG. 7, which positions are defined by engagement of the flat side 69 of extension 57 with the stop pin 54. Referring to FIGS. 6 and 7, it is seen that in the solid line position of the reversing valve 56, air from the inlet passage 66 and bore 67 is directed through the valve plate passage 51 to one of the motor air passages 43. At the same time, exhaust air from the second motor air passage 43 is directed through the valve plate passage 52 into exhaust chamber 58 and rearwardly through the exhaust air passage 68. In the reversed or dotted line position of the reversing valve 56 (FIG. 7) inlet air from passages 66 and 67 is directed to the motor through valve plate passage 52 and exhaust air travels through valve plate passage 51 to the exhaust chamber 58 and exhaust passage 68. The reversing valve 56 is pivoted between dotted line and solid line positions therefore by manually rotating an externally tapered end cap 71 which is in a press fit with the cylindrical rear extension 72 of the reversing valve 56.

Pressurized air is delivered to the central inlet passage 66 of reversing valve 56 through an elongated tube 73 (FIG. 3) fitted onto the barbed end 74 of an inlet fitting 76, for the passage 66.

An annular diffuser element 78 is inserted into the open rear end of the end cap 71 and about the inlet tube 73 so as to clamp the tube on the barbed end 74 of inlet fitting 76. Thus exhaust air from the passage 68 enters an annular exhaust chamber 79 formed about the inlet fitting 76 for exhaust to the atmosphere through the diffuser element 78. The diffuser element 78 is formed of a cindered material to both diffuse the high pressure exhaust air and to muffle exhaust noise.

The reversing valve 56 and air motor 24 may be lubricated without disassembly of the handpiece 20 due to the provision of small radial bores 81 and 82, FIG. 5, through the end cap 71 and reversing valve 56, respectively. These bores are aligned to form an external oil port opening into a longitudinal bore 83 in the reversing valve 56, which bore 83 opens at its forward end into the inlet passage 67. A flexible tubular seal 84 and a solid resilient plug 86 are inserted into the rear end of bore 83 as shown. Thus, referring to FIGS. 5 and 8, the tip 87 of an oil delivery spout is insertable into the oil port to collapse the tubular seal 84 and introduce oil into the inlet passage 67. Incoming air from the passage 66 carries the oil through passages 67 and 51 to the motor 24.

Figure 4:
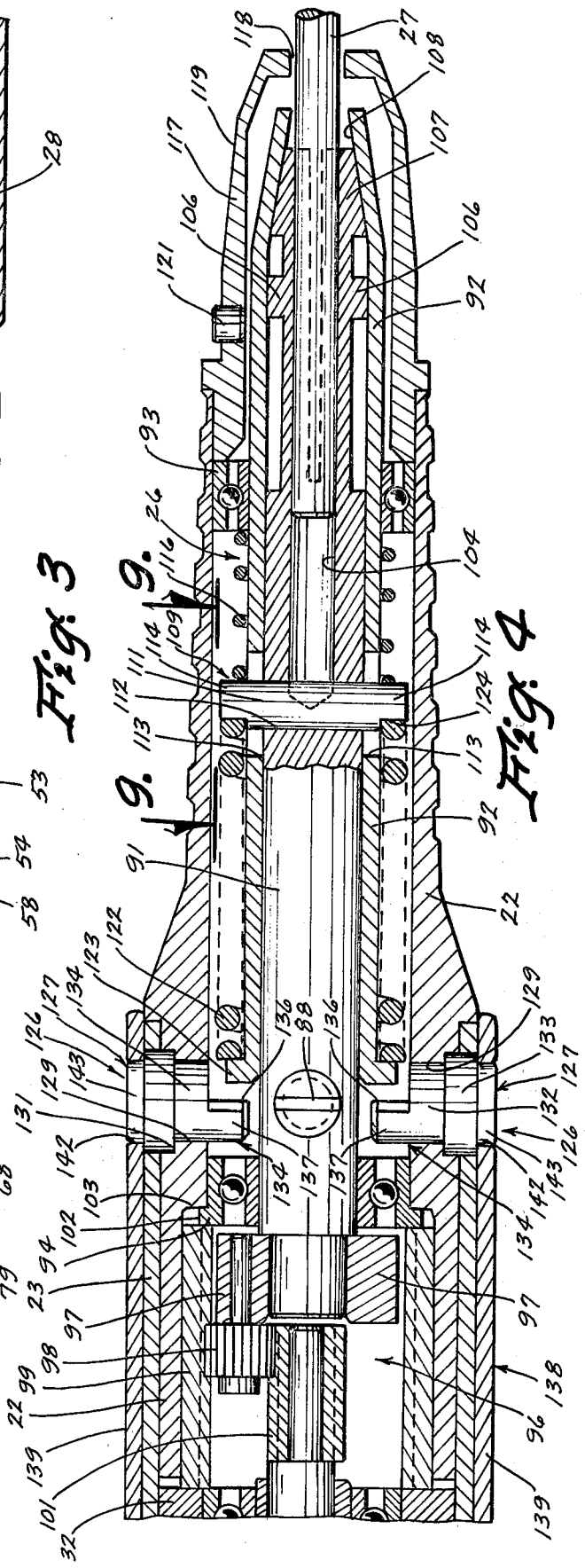
FIG. 4 is an enlarged longitudinal sectional view of the front section of the handpiece, as seen on line 4—4 in FIG. 2.

Referring now to the forward end of the handpiece 20, and as seen in FIG. 4, the forward housing portion 22 is telescopically received within the rear housing portion 23. The housing portions are secured together by a screw 88, (shown superimposed in FIG. 4), to prevent relative axial and rotational movement therebetween.

The collet mechanism, referred to generally at 26, includes an elongated collet shaft 91 and a collet receiving sleeve 92 telescopically mounted on the collet shaft 91 for relative axial movement. The collet shaft and sleeve assembly is rotatably supported within the forward housing portion 22 by front and rear collet bearings 93 and 94, respectively. Whereas the collet sleeve 92 is freely slidable axially within the front bearing 93, the collet shaft 91 is locked against axial movement by a press fit relation within the rear collet bearing 94.

The collet shaft 91 is connected in driven relation with the motor 24 by a gear reduction mechanism, indicated generally at 96 in FIG. 4, which includes an annular planet gear carrier 97 fixed on the rear end of the collet shaft 91 and having three circumferentially spaced planet gears 98. Each planet gear 98 is in meshed relation with an internal ring gear 99 and an external sun gear 101 fixed on the forward end of the rotor 34. The mechanism 96 effects a four to one reduction in the speed of rotation of the rotor 34 relative to the collet shaft 91.

To secure the collet shaft 91 against axial movement within the housing 21, the rear collet bearing 94 is provided with an external annular flange 102 positioned between the ring gear 99 and an internal annular shoulder 103 on the forward housing portion 22. The rear end of the ring gear 99 abuts the front motor bearing housing 32.

The forward end of the collet shaft 91 has a burr receiving axial bore 104 (FIG. 4) having a forward side wall section formed with a plurality of longitudinally extended circumferentially spaced radially yieldable fingers 106. The free ends of the yieldable fingers 106 have forwardly tapered external bearing surfaces 107 frictionally engageable with a mating tapered internal bearing surface 108 at the forward end of the collet receiving sleeve 92. The tapered bearing surfaces 107 and 108, in response to a rearward axial movement of the collet receiving sleeve 92, move the yieldable fingers 106 radially inwardly into frictional engagement with a burr 27 received in the bore 104. In response to a forward axial movement of the collet receiving sleeve 92, the yieldable fingers 106 are permitted to move radially outwardly to release the burr 27.

The collet shaft 91 and collet receiving sleeve 92 are coupled for rotation as a unit with limited relative axial movement by the provision of a pin and slot connection, indicated generally at 109 in FIGS. 4 and 9. This lost motion connection 109 includes a pin 111 extended within a diameteric bore 112 in a medial portion of the collet shaft 91 and through a pair of diametrically opposed axially extended slots 113 in the collet receiving sleeve 92. The pin 111 is of a length such that its terminal end portions 114 project outwardly of the collet receiving sleeve 92 for termination within the forward housing portion 22, so as to be freely rotatable with the collet mechanism 26.

A light preload spring 116 is mounted about the collet receiving sleeve 92 forwardly of the pin 111 to yieldably retain the front collet bearing 93 against the rear end of a nose cone 117 that is positioned within the open front end of the forward housing portion 22. Nose cone 117 has a central opening 118 through which the dental burr 27 is received in the collet mechanism 26. The forwardly tapered peripheral surface 119 of the nose cone 117 and a cylindrical key 121 seated therein are adapted to receive in a nested relation thereon the neck portion of a contra angle unit (not shown) when the drive shank of the contra angle unit is inserted into the collet mechanism in place of the burr 27.

A heavy collet spring 122, mounted on the collet receiving sleeve 92 is arranged in compression between the terminal ends 114 of the pin 111 and an external annular flange 123 at the rear end of the collet receiving sleeve 92. Collet spring 122 thus acts on the collet receiving sleeve 92 to bias the yieldable fingers 106 radially inwardly to the closed burr gripping positions therefor shown in FIG. 4. The terminal end portions 114 of the pin 111 are notched as at 124 so that the pin 111 is held against movement transversely of the collet shaft 91 by the forward end of the collet spring 122.

A cam mechanism, indicated generally at 126 in FIG. 4, is provided for actuating the collet mechanism 26 and includes a pair of generally cylindrical cams 127 rotatably received within diametrically opposite bores 128 formed in the housing 21. Each bore has an inner section 129 and an outer section 131 of enlarged diameter.

Each cam 127 (FIG. 10) has a medial hub portion 132 rotatable within the inner bore section 129 and an external annular bearing shoulder 133 rotatable within the outer portion 131. A generally semicylindrical shaped terminal end portion 134 on each cam 127 extends inwardly of the housing from the hub portion 132 for termination in a clearance relation with the collet shaft 91, as seen in FIG. 4.

Each terminal end portion 134 of a cam 127 has a flat surface 136 and an arcuate cam surface 137. When a burr 27 is within the collet mechanism 26, the flat surfaces 136 of the cams 127 are in a clearance relation with the collet receiving sleeve flange 123. However, it is seen that as the cams 127 (FIG. 11) are rotated, the arcuate cam surfaces are moved into engagement with the flange 123 whereby the collet receiving sleeve 92 is axially moved against the action of the heavy collet spring 122. The flange 123 thus constitutes the cam follower means for the cam mechanism 126.

Leverage for rotating the cams 127 is provided by an external actuator lever 138, shown in FIGS. 2 and 12. The one piece lever 138 has a pair of elongated legs 139 connected together at one end by a saddle member 141. The opposite or free end of each leg 139 has a longitudinal slot 142 for receiving an upstanding stub shaft 143 on the outer end of each cam 127. To install the lever 138, the legs 139 are spread apart and snapped into a press fit engagement with the stub shafts 143. The tendency of the legs 139 to move toward each other serves to retain the cams 127 within the bores 128 and to connect the cams 127 for unit rotation.

With a burr 27 received within the collet mechanism 26, the lever 138 is moved to its operating position, as shown in solid lines in FIG. 2, extended generally longitudinally of and in nested engagement with the housing 21. In FIG. 12, it is seen that the inner surfaces of the legs 139 are somewhat concave in cross section and thereby exert a light spring grip on the housing to retain the lever 138 in its operating position. To release the burr 27, the lever 138 is pivotally moved from its operating position to a collet opening position, shown in dotted lines in FIG. 2. Referring to FIG. 11, the pivotal movement of the lever 138, to the collet opening position therefor, effects approximately a one hundred and eighty degree rotation of the cams 127, whereby the cam follower flange 123 and collet receiving sleeve 92 are moved forwardly to release the burr 27. In the collet opening position for the lever 138, it can be seen that the reactive force exerted by the cam follower flange 123 against the cams 127 is applied in a plane extended through the axes of the cams 127 so as to eliminate any tendency of the lever 138 to snap out of its collet opening position.

When a burr 27 is received into the collet mechanism 26, the pivot lever 138 is readily moved to its operating position in nested engagement with the housing 21, for the performance of subsequent dental procedures.

Although the invention has been described with respect to a preferred embodiment thereof, it is to be understood that it is not to be so limited since changes and modifications can be made therein which are within the full intended scope of this invention as defined by the appended claims.

We claim:

1. A dental handpiece having a tubular housing with forward and rearward end portions and a motor supported in said housing, comprising:
    (a) a burr receiving collet mechanism rotatably supported within said forward portion, including an elongated collet shaft connected at one end in a driven relation with the motor,
    (b) said collet shaft having a plurality of circumferentially spaced and radially yieldable fingers longitudinally extended from the other end thereof,
    (c) a collet receiving sleeve telescopically mounted on said collet shaft for relative axial movement,
    (d) coacting means on said collet shaft and collet receiving sleeve, responsive to axial movement of the sleeve in one direction to move said yieldable fingers radially inwardly and responsive to axial movement of the sleeve in the opposite direction to permit said fingers to move radially outwardly,
    (e) bias means urging the collet receiving sleeve in said one direction,
    (f) a cam means supported on the housing for rotation about an axis extended transversely of the housing, said cam means having a cam surface arranged internally of the housing,
    (g) cam follower means on said collet receiving sleeve for moving the collet receiving sleeve in said opposite direction in response to rotation of said cam means,
    (h) lever means externally of the housing for actuating said cam means,
    (i) said cam means includes a pair of cams spaced transversely of the housing, and
    (j) means connecting said lever means to said pair of cams for concurrent actuation,
    (k) said pair of cams having like cam surfaces engageable with respective portions of said cam follower means to move the collet sleeve in said opposite direction.

2. The dental handpiece, according to claim 1, wherein:
    (a) said housing has a pair of diammetrically opposed bores therethrough,
    (b) each cam having a generally cylindrical medial hub portion rotatably receivable in a respective one of said bores and an annular bearing shoulder outwardly of the hub portion rotatably seated on said housing, and
    (c) said cams retained within the housing bores by said lever means.

3. The dental handpiece, according to claim 1, wherein:
    (a) said lever means includes a unit body lever of a generally U-shape having a base and a pair of elongated legs, each of which has a free end connected to a respective cam, and said lever being of an arcuate shape in transverse cross section so as to be movable from an operating position extended generally longitudinally of and in nested engagement with said housing to a collet opening position projected generally radially of the housing.

4. The dental handpiece, according to claim 3, wherein:
   (a) said cam surfaces are disengaged from the cam follower means when said lever is in its operating position, and
   (b) said cam surfaces, in response to pivotal movement of said lever from the operating position to the collet opening position therefor, being engageable with said cam follower means to axially move the collet receiving sleeve in said opposite direction.

5. The dental handpiece, according to claim 1, wherein:
   (a) the collet sleeve has a pair of diametrically opposed axially extended elongated slots therein,
   (b) said collet shaft has a bore extended diametrically therethrough, and
   (c) a pin extended through said bore and slots for rotatively coupling the collet shaft and collet receiving sleeve for limited relative axial movement therebetween.

6. The dental handpiece, according to claim 5, wherein:
   (a) said cam follower means comprises an outwardly directed projection on the collet receiving sleeve,
   (b) said pin includes opposite end portions extended radially outwardly from the collet receiving sleeve, and
   (c) said bias means comprises a compression spring positioned about the collet sleeve and arranged in compression between said projection and the opposite end portions of said pin.

* * * * *